(12) United States Patent
Wigginton et al.

(10) Patent No.: US 11,266,454 B2
(45) Date of Patent: Mar. 8, 2022

(54) WIRE TENSIONER WITH SWIVEL HINGE

(71) Applicant: New Standard Device, LLC, San Anontio, TX (US)

(72) Inventors: Robert E. Wigginton, McKinney, TX (US); Bryant T. Phamvu, San Antonio, TX (US); C. Douglas Klein, Jr., Andover, MA (US)

(73) Assignee: New Standard Device, LLC, San Antonio, TX (US)

( * ) Notice: Subject to any disclaimer, the term of this patent is extended or adjusted under 35 U.S.C. 154(b) by 8 days.

(21) Appl. No.: 16/373,833

(22) Filed: Apr. 3, 2019

(65) Prior Publication Data

US 2019/0223933 A1 Jul. 25, 2019

(51) Int. Cl.
  *A61B 17/88* (2006.01)
  *A61B 17/66* (2006.01)
  *A61B 17/56* (2006.01)

(52) U.S. Cl.
  CPC .......... *A61B 17/8869* (2013.01); *A61B 17/66* (2013.01); *A61B 17/88* (2013.01); *A61B 17/8861* (2013.01); *A61B 2017/564* (2013.01)

(58) Field of Classification Search
  CPC ..... A61B 17/66; A61B 17/88; A61B 17/8861; A61B 17/8869; A61B 2017/90
  See application file for complete search history.

(56) References Cited

U.S. PATENT DOCUMENTS

| | | | | |
|---|---|---|---|---|
| 5,057,113 A | * | 10/1991 | Mingozzi | A61B 17/8869 606/103 |
| 5,431,659 A | * | 7/1995 | Ross, Jr. | A61B 17/8869 140/123.5 |
| 9,023,045 B2 | * | 5/2015 | Lehmann | A61B 17/62 606/56 |
| 9,445,841 B2 | * | 9/2016 | Samchukov | A61B 17/62 |
| 9,936,975 B2 | * | 4/2018 | Siemer | A61B 17/6416 |
| 2019/0119064 A1 | * | 4/2019 | Wong | A61B 17/62 |

* cited by examiner

*Primary Examiner* — Zade Coley
*Assistant Examiner* — Diana Jones
(74) *Attorney, Agent, or Firm* — Gregory K. Goshorn; Greg Goshorn, P.C.

(57) ABSTRACT

Provided is a device for tensioning a wire in conjunction with an external bone fixation (EBF) device. A swivel hinge body comprises two forks extending in a plane parallel from the swivel hinge body. A lower lip extends from the swivel hinge body below and in parallel with the two forks. A swivel pin and a swivel block are positioned between the lower lip and the plane of the two forks and held in place by the swivel pin such that the swivel block is able to rotate in an arc with respect to the lower lip and the swivel hinge body. The swivel block comprises a face, wherein the face is configured to fit against an edge of a component of the EBF device such that, when the tensioning mechanism is applying tension to the wire, the swivel hinge body is prevented from deflecting to one side.

12 Claims, 7 Drawing Sheets

US 11,266,454 B2

WIRE TENSIONER WITH SWIVEL HINGE

FIELD OF THE DISCLOSURE

The claimed subject matter relates generally to a wire tensioner with a swivel hinge for use in conjunction with an external bone fixation device that uses small diameter wires and, more specifically, tensioner with a swivel hinge for attaching and tightening wires in an external bone fixation device.

BACKGROUND

External Bone Fixation (EBF) devices are employed in the treatment of bone deformity and acute trauma. Typically, some EBF devices use hardware, typically including circular rings or open plates, that surround a patient's limb. Adjustable connection rods and struts are employed to connect the hardware together. Pins and small diameter wires are employed to attach the plates to a patient's bone to stabilize the bone while the bone or bones are being corrected or healing. The wires typically attach to the EBF device at two points and are inserted through a bone using a power drill. Correctly inserting the wire through the bone and attaching it on both sides of the EBF device is important for stability. Preferably, the wire is placed where it lies on the plate of the EBF device although the wire may be inserted at an angle to an edge of the plate. It should be understood that EBF plates come in a wide variety of configurations, including but not limited to 'C' shaped, 'N' shaped, 'J' shaped, 'K' shaped plates and so on.

Current devices that attach wires to an EBF device may fit flat on the edge of a ring, plate, foot plate or post of the EBF device although attached wires or pins may cross the edge of a ring, plate, foot plate or post at an angle. When a wire tensioner is installed on the wire that crosses at an angle other than ninety degrees (90°), the angle may cause the tensioner to cock to one side, thereby bending the wire while the wire is being tensioned.

One well-known reconstructive EBF system is the Ilizarov frame, as shown in U.S. Pat. Nos. 4,365,624; 4,615,338; 4,978,348, 5,702,389 and 5,971,984. The Ilizarov frame uses a combination of circular frames, pins and wires for deformity correction of the bone.

SUMMARY

Provided is a swivel hinge wire tensioner, or simply "swivel hinge tensioner," for use in conjunction with an external bone fixation (EBF) device. The disclosed swivel hinge tensioner is employed to attach wires to rings, plates, foot plates and posts on an EBF device. Since, attached wires may cross the edge of a ring, plate, foot plate or post at an angle, a current wire tensioner on the wire may be cocked to one side, thereby bending the wire and making the tensioner unstable and displacing the bone segment. A swivel bar in the disclosed swivel hinge enables the swivel hinge to be set at any angle to improve control of the tensioning.

Provided is a device for tensioning a wire in conjunction with an external bone fixation (EBF) device comprising a swivel hinge body configured to be coupled to a tensioning mechanism, the swivel hinge body comprising two forks extending in a plane parallel from the swivel hinge body; and a lower lip extending from the swivel hinge body below and in parallel with the two forks; a swivel pin; and a swivel block positioned between the lower lip and the plane of the two forks and held in place by the swivel pin such that the swivel block is able to rotate in an arc with respect to the lower lip and the swivel hinge body, the swivel block comprising a swivel block face; wherein the swivel block is configured to fit against an edge of a component of the EBF device such that, when the tensioning mechanism is applying tension to the wire, the swivel hinge body is prevented from deflecting from an angle formed by the wire and the edge.

Also provided is a tensioning device for tensioning a wire in conjunction with an external bone fixation (EBF) device comprising a tensioning mechanism and the disclosed swivel hinge.

This summary is not intended as a comprehensive description of the claimed subject matter but, rather, is intended to provide a brief overview of some of the functionality associated therewith. Other systems, methods, functionality, features and advantages of the claimed subject matter will be or will become apparent to one with skill in the art upon examination of the following figures and detailed description.

BRIEF DESCRIPTION OF THE DRAWINGS

A better understanding of the claimed subject matter can be obtained when the following detailed description of the disclosed embodiments is considered in conjunction with the following figures.

DETAILED DESCRIPTION OF THE FIGURES

The illustrations and diagrams in the Figures illustrate the architecture, functionality, and operation of possible implementations of systems according to various embodiments of the present invention.

Figure 1:
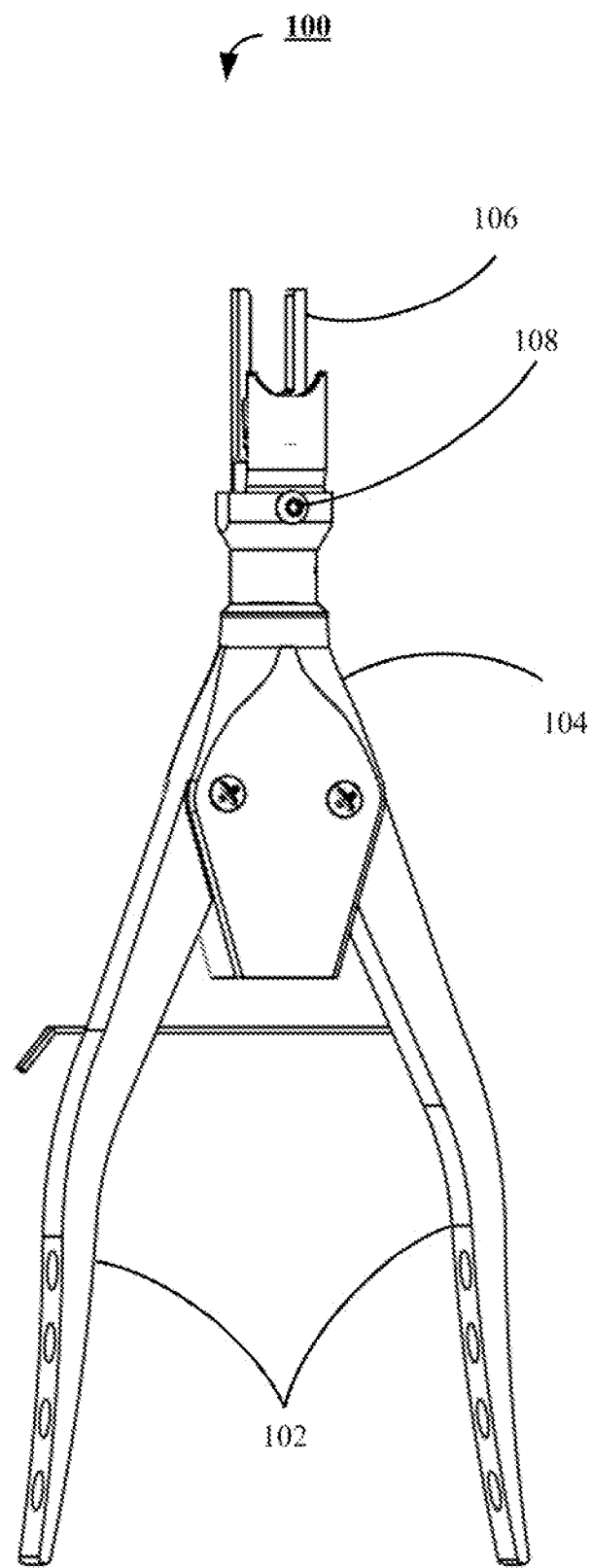
FIG. 1 is an illustration of a swivel hinge wire tensioner accordance with the claimed subject matter.

FIG. 1 is an illustration of a wire tensioner device, or simply "tensioner" 100 that incorporates a swivel hinge in accordance with the claimed subject matter. Tensioner 100 includes two (2) handles 102, a tensioner body 104 and a swivel hinge 106. Swivel hinge 106 slips into tensioner body 104 and is secured with a screw 108. Handles 102 are moved from an open to a closed position to pull on a wire (see 208, 234, 236, FIG. 7) passing through body 104 and swivel hinge 106. After nut 174 is tightened and handles 102 are moved from a closed to an open position, tensioner 100 advances the mechanism that secures the wire without any existing tension on the wire being released or disrupting the alignment of the wire with respect to the a EBF hardware (see 200, FIG. 7). In this manner, tension on the wire may be "ratcheted up" by opening and closing handles 102. After the wire is tensioned, nut 180 is tightened securing the tensioned wire to a ring, plate or post (see 152, 220, 224 and 228, FIG. 7) and tensioner 100 can be released from the wire and removed.

The ratcheting mechanism of handles 102 and body 104 should be familiar to those with skill in the appropriate arts. It should also be understood that handles 102 and body 104 are only one example of tensioner mechanisms that may be used in conjunction with swivel head 106. Devices that create tension on a wire employing rotary dials rather than handles are also available and would work equally well with swivel hinge 106. For example, some tensioner devices wrap a wire around a post, wire fixation bolt or nut and apply tension to the wire by rotating the post, bolt or nut.

Figure 2:
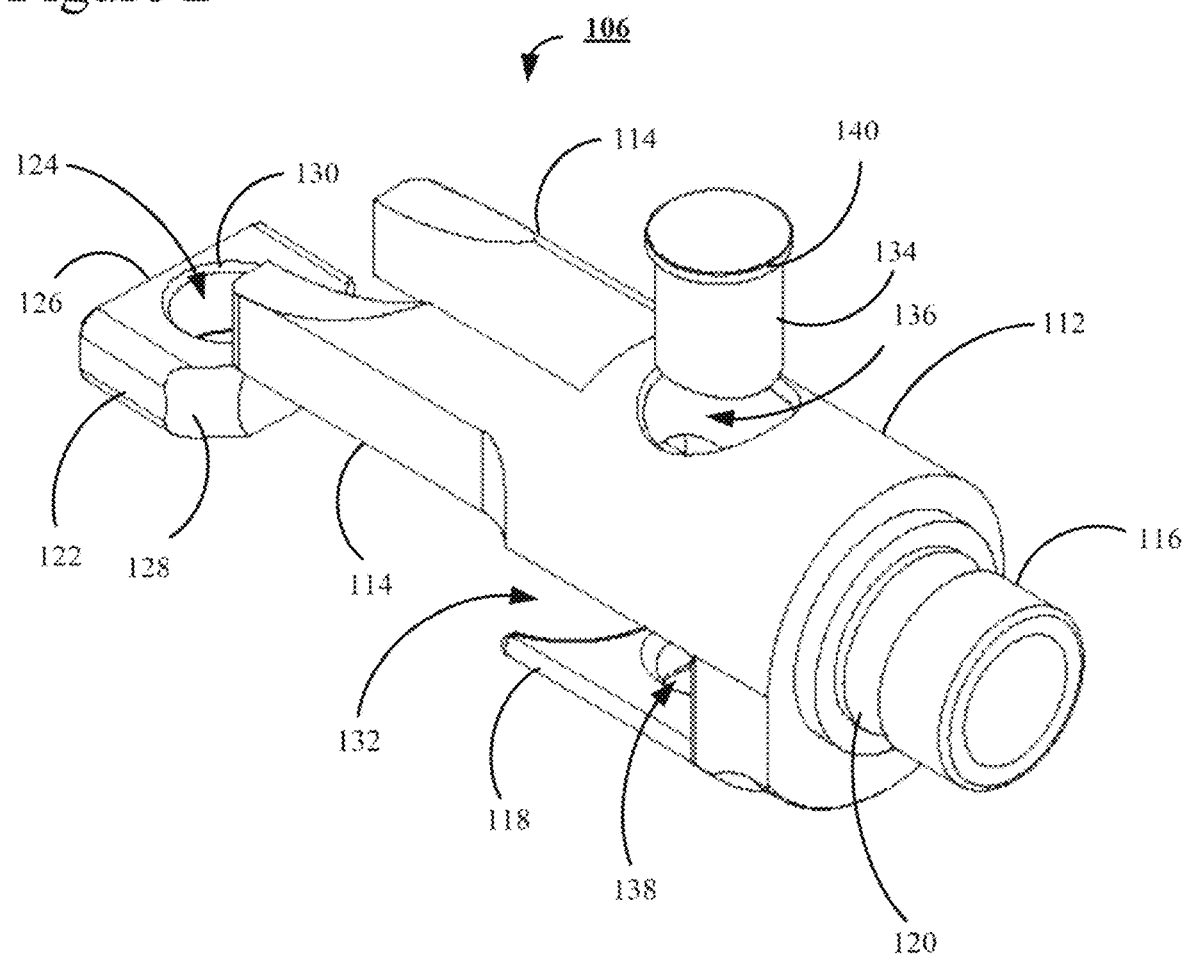
FIG. 2 is an illustration of the swivel hinge of the wire tensioner of FIG. 1 disassembled and in more detail.

FIG. 2 is an illustration of disassembled swivel hinge, or simply "hinge," 106 of FIG. 1 in more detail. Hinge 106 includes a body 112 that itself includes two (2) extensions, or "forks," 114, a nipple 116 and an extension 118 that is parallel to forks 114. Nipple 116 fits into a tensioner body such as body 104 (FIG. 1) and is secured to body 104 with a screw (not shown) that is threaded through body 104 and is tightened into a groove 120 at the base of nipple 116.

A swivel block 122 includes a hole 124, a face 126 and two (2) bevels 128, only one of which is visible in FIG. 2, on a side of swivel block 122 opposite face 126. Hole 124 includes a small bevel 130 on a top surface of swivel block 122.

Swivel block 122 fits through an opening 132 in body 112 and is secured with a pin 134 that passes completely through body 112 via a hole 136, then through hole 124 of swivel block 122 and is pressed into a second hole 138 in body 112. A lip 140 of pin 134 is slightly larger than the rest of the diameter of pin 134. Hole 136 has a diameter large enough to enable pin 134, including lip 140, to pass. Hole 138 has a diameter large enough to enable pin 134 but not lip 140 to pass. Pin 134 is pressed into hole 138 until lip 140 is secured into bevel 130 of swivel block 122. Hole 124 of swivel block 122 has a diameter large enough to enable swivel block 122 to swivel back and forth until bevels 128 abut body 112 in opening 132. In one embodiment, pin 134 is pressed fitted into hole 138, pin 134 is welded in place and then ground smooth and polished to for the configuration of body 112.

Figure 3:
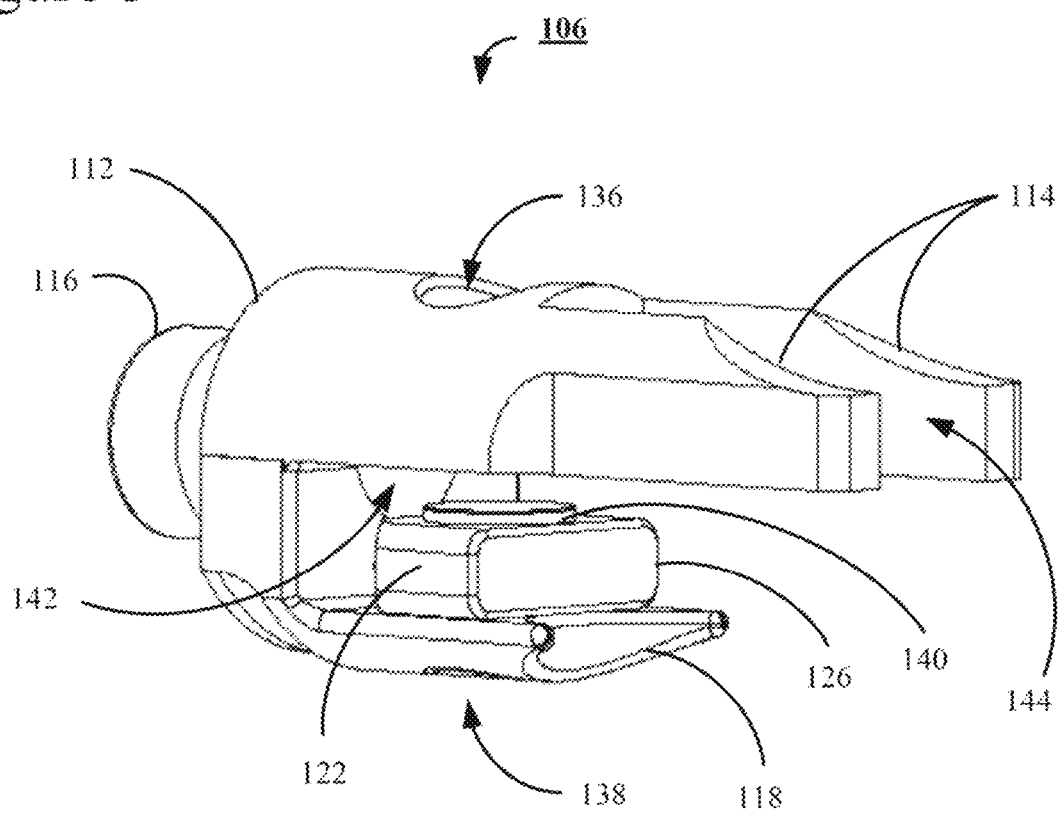
FIG. 3 is an illustration of the swivel hinge wire tensioner of FIG. 2 assembled and from a different perspective.

FIG. 3 is an illustration of swivel hinge 106 of FIG. 2 both assembled and from a different perspective. Included in FIG. 3 are swivel hinge body 112, nipple 116, extension 118, forks 114, swivel block 122, swivel block face 126, holes 136 and 138 in body 112 and lip 140 of pin 134, which is obscured, all of which were introduced above in conjunction with FIG. 2. Swivel hinge 106 is assembled in that swivel block 122 has been installed in body 112 of swivel hinge 106 by pressing pin 134 through swivel block 122 and into hole 138 and then welded around hole 138 to hold pin 134. A hole 142 passes through body 112, including nipple 116. Hole 142 and an opening 144 in body 112 between forks 114, and the utility associated with these particular elements, are described below in conjunction with FIGS. 5 and 6.

Figure 4:
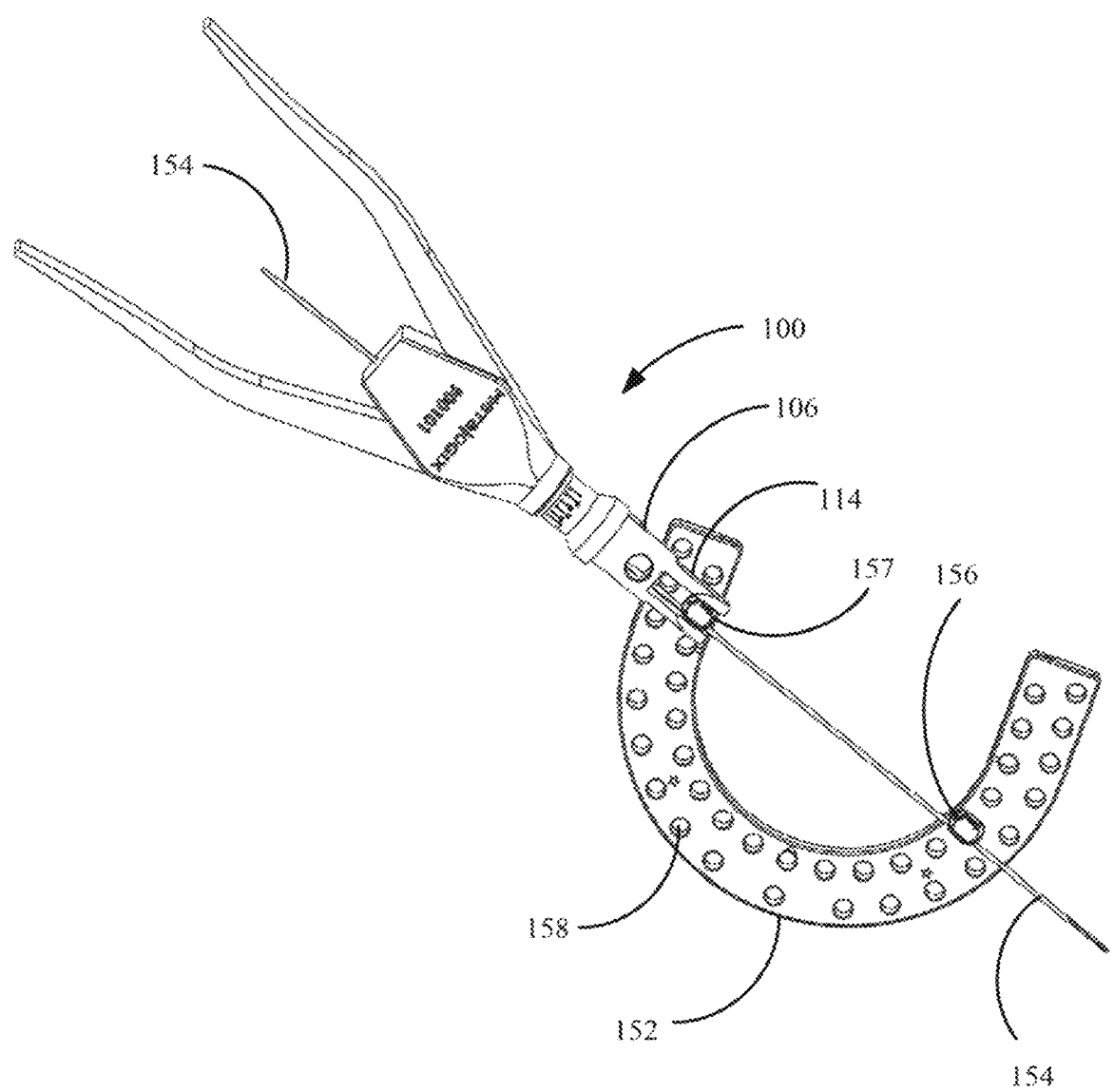
FIG. 4 is an illustration of the swivel hinge wire tensioner of FIG. 1 positioned to affix a wire to a fixation plate of an External Bone Fixation (EBF) device.
Figure 6:
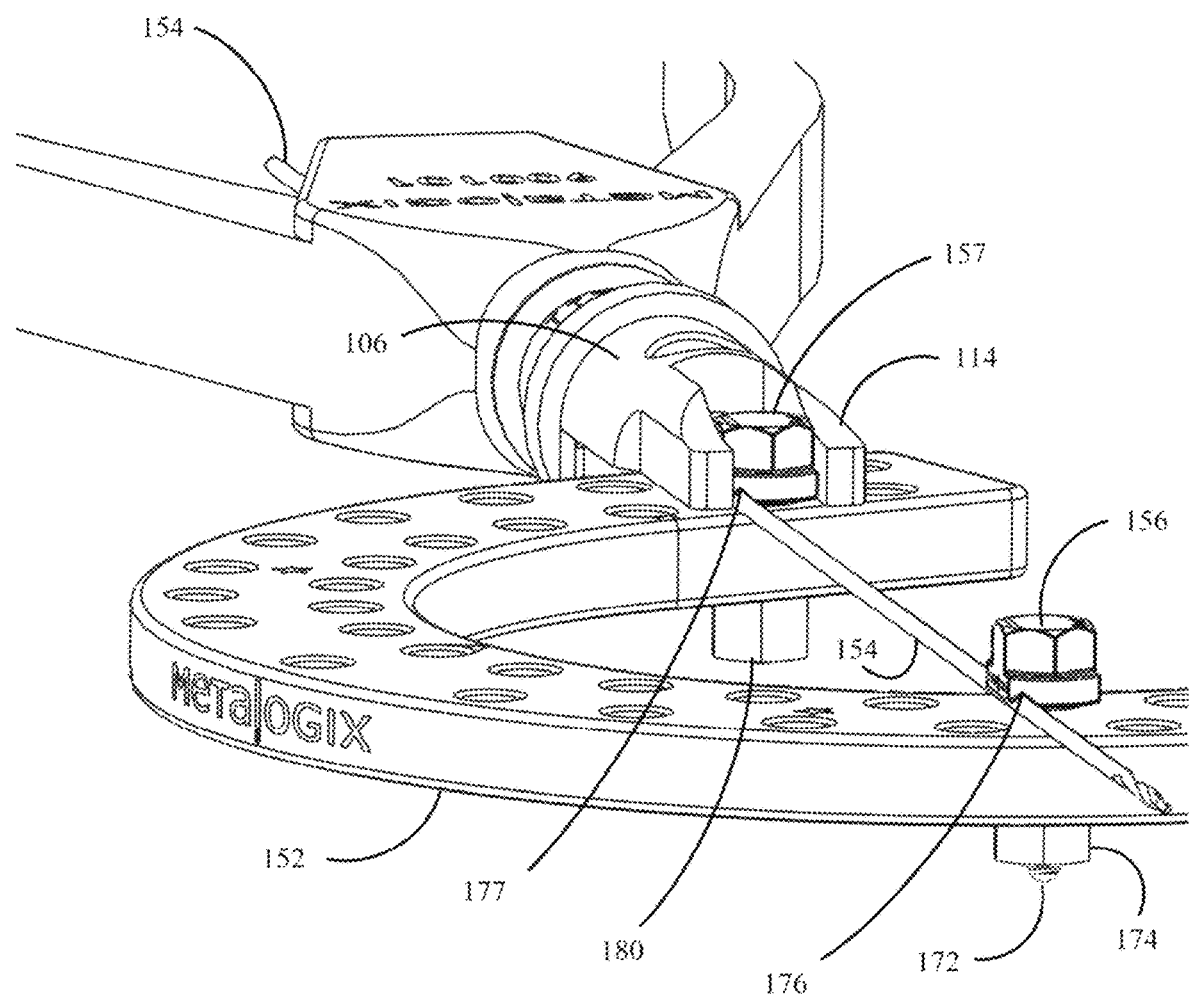
FIG. 6 is an illustration of the swivel hinge of the wire tensioner of FIGS. 1-5 attached to the fixation plate of FIGS. 3 and 4 in a different position than that of FIG. 4 and showing aspects that are obscured in FIGS. 4 and 5.
Figure 7:
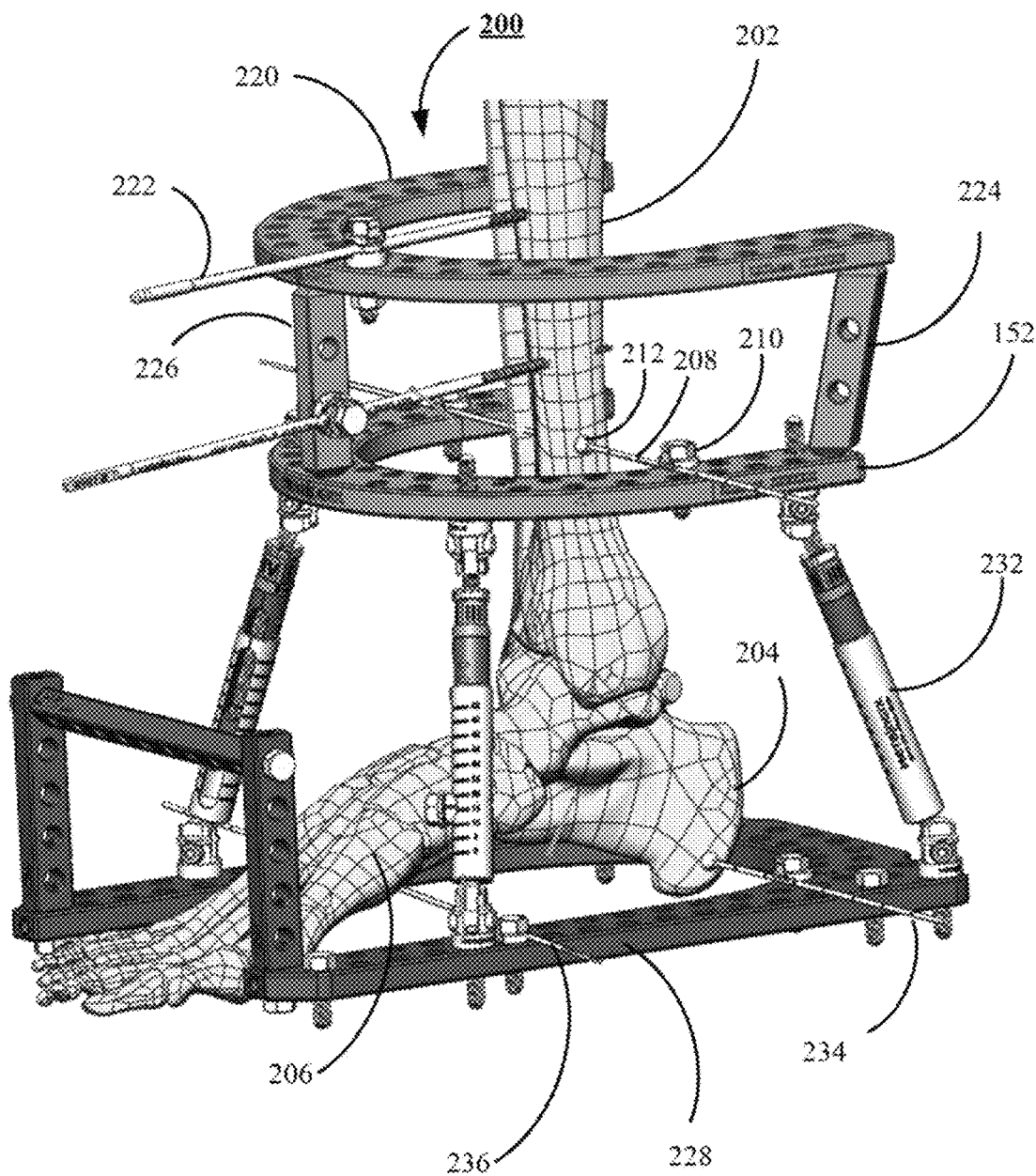
FIG. 7 is an illustration of an External Bone Fixation (EBF) device that employs the swivel hinge wire tensioner of FIGS. 1-6.

FIG. 4 is an illustration of swivel hinge wire tensioner 100 of FIG. 1 attached to a fixation plate 152 of an External Bone Fixation (EBF) device (see 200, FIG. 7). Included in FIG. 4 are swivel hinge 106 (FIGS. 1-3) and forks 114. Tensioner 100 is in position to tighten an orthopedic wire 154, which passes through swivel hinge 106 and, in this example, can be viewed extending through tensioner 100. On one end, wire 154 is held in place on plate 152 by means of a wire fixation bolt, or simply "fixation bolt," 156, which is tightened before any tension is applied. On the other end, wire 154 is held in place by a fixation bolt 157, which is tightened once an appropriate amount of tension has been applied to wire 154 by tensioner 100. Fixation bolt 157 fits within a gap between forks 114 such that fixation bolt 157 is prevented from turning while tensioner 100 is employed installing wire 154. It should be noted that in the illustrated embodiment, forks 114 are long enough to reach fixation bolt 157, which is positioned in a second, or inner, row holes in plate 152. Each of fixation bolts 156 and 157 positioned through one of a number of holes 158 in plate 152, only one of which is labeled for the sake of simplicity, and secure wire 154 when fixation nuts (see 174, 180, FIG. 6) are tightened.

Figure 5:
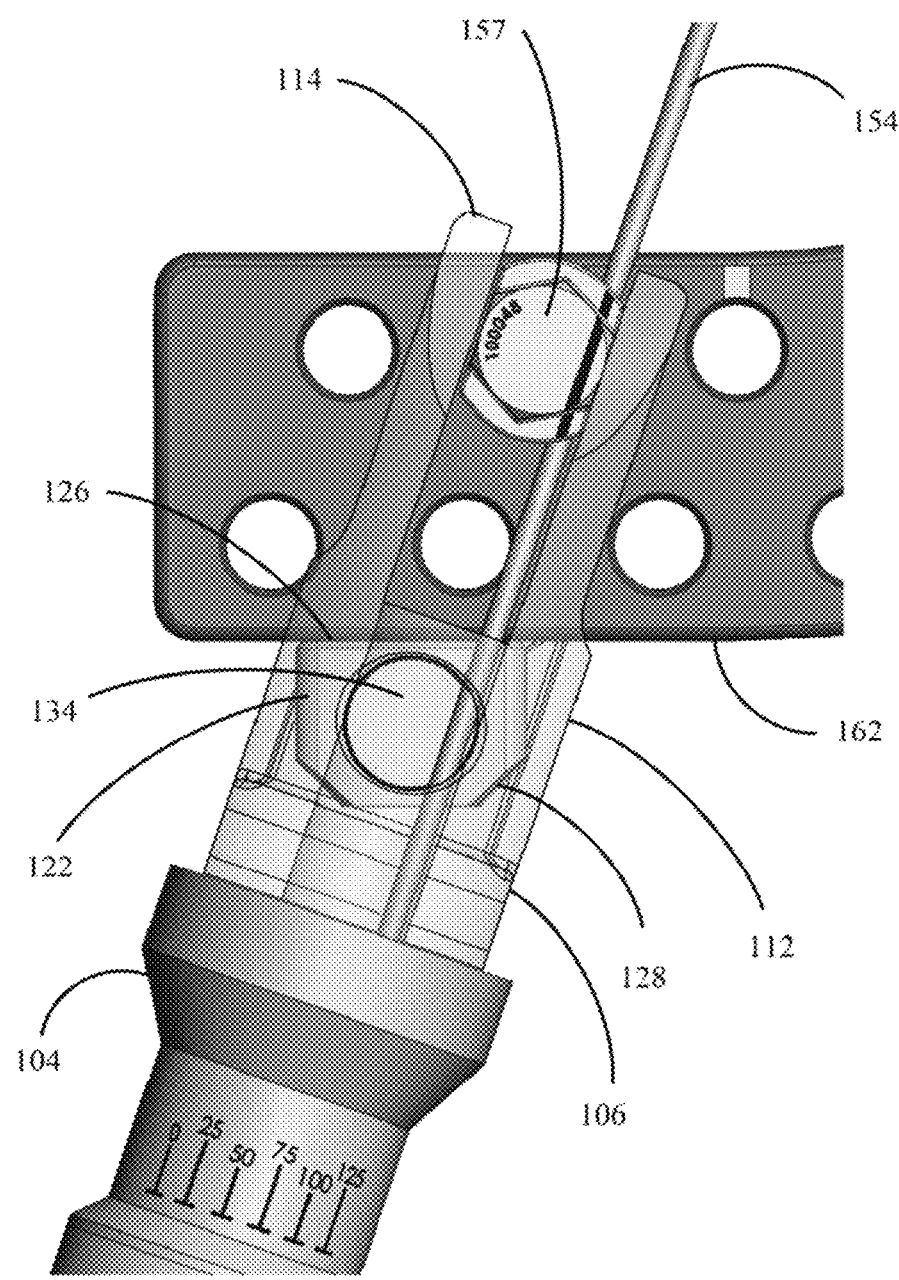
FIG. 5 is a close up illustration of the swivel hinge of the wire tensioner of FIGS. 1-4 attached to the fixation plate of FIG. 4 that shows elements of the swivel hinge that are typically obscured.

FIG. 5 is an illustration of swivel hinge 106 (FIGS. 1-4) of wire tensioner 100 (FIG. 1) attached to a fixation plate 162 in a different position than the position in FIG. 4 and that shows elements of swivel hinge 162 that are typically obscured. Swivel hinge 106, which is attached to tensioner body 104 (FIG. 1), includes body 112, swivel block 122 and face 126, all of which were illustrated in FIGS. 2-3. Also shown are forks 114 (FIGS. 2-4) and bevel 128 (FIG. 2). In this figure, face 126 of swivel block 122 fits flush against and edge of plate 162. Bevel 128 provides clearance between swivel block 122 and body 112. Pin 134 enables swivel block 122 to rotate so that face 126 may fit flush against plate 162 when wire 154 is positioned at an angle between approximately forty-five and ninety degrees (45-90°) with respect to the edge of plate 162. In this manner, tensioner 100 (FIG. 1) is able to apply tension to wire 154 (FIG. 4 without the tension pulling tensioner 100 to an angle to one side with respect to wire 154. Forks 114 prevent fixation bolt 157 (FIG. 4) from turning when nut 180 (see FIG. 6) is tightened.

FIG. 6 is an illustration of swivel hinge 106 of FIGS. 1-5 of wire tensioner 100 of FIG. 1 attached to plate 152 of 4 from a different perspective showing aspects that are obscured in FIGS. 4 and 5. Visible in FIG. 6 are swivel hinge 106, forks 114, fixation plate 152, wire 154 and fixation bolts 156 and 157. Also visible in FIG. 6 is an end 172 of fixation bolt 156 and a nut 174 that threads onto fixation bolt 156 to secure fixation bolt 156 to plate 152. Although not visible in FIG. 6, fixation bolts 156 and 157 fit through holes such as hole 158 (FIG. 4) in plate 152. Visible in bolts 156 and 157 are notches 176 and 177, respectively, that enable wire 154 to pass and be secured when nut 174 and a corresponding nut 189 on fixation bolt 157 are tightened. Although not apparent in FIG. 6, it should be noted that gap 132 (FIG. 2) between forks 114 and extension 118 (FIGS. 2-3) is wide enough for plate 152 to fit.

FIG. 7 is an illustration of an External Bone Fixation (EBF) device 200 affixed to a patient's leg (not shown), which includes a leg bone 202, a heel bone 204 and a foot bone 206. Swivel hinge wire tensioner 100 of FIGS. 1-6, which is not shown in FIG. 7, has been employed to place an appropriate amount of tension on an orthopedic wire 208, like wire 154 (FIGS. 4 and 6), which is attached to EBF device 200 with a fixation bolt 210 like fixation bolt 156 (FIGS. 4 and 6). In this example, a truss 212 affixed to wire 208 prevents leg bone 202 from moving in frame 200. Wire 208 passes through leg bone 202 and is secured, prior to tensioning, to an opposing side of plate 152 by another fixation bolt such as fixation bolt 156 (FIGS. 4 and 6).

A second plate 220 is secured to leg bone 202 with an orthopedic pin 222 and to plate 152 with posts 224 and 226. Typically, a third post that is not visible in FIG. 7 would also connect plate 220 to plate 152. Post 226 is also attached to leg bone 202 with a pin and fixation bolt (not labeled).

Plate 152 is affixed to a foot plate 228 with four adjustable struts 232, only one of which is labeled and three of which are visible in FIG. 7. Two wires 234 and 236 secure foot plate 228 to ankle bone 204 and that bone 206 respectively. Wires 234 and 236 would be installed employing tensioner 100 in accordance with the disclosed technology. It should be understood that wires, which may also attach to posts such as posts 224 and 226 and to bones such as 202, 204 and 206, may be tensioned with the disclosed technology.

While the claimed subject matter has been shown and described with reference to particular embodiments thereof, it will be understood by those skilled in the art that the foregoing and other changes in form and detail may be made therein without departing from the spirit and scope of the claimed subject matter, including but not limited to additional, less or modified elements.

We claim:

1. A device for tensioning a wire in conjunction with an external bone fixation (EBF) device, comprising:
   a tensioning mechanism for applying tension to a wire;
   a swivel hinge body coupled to the tensioning mechanism, the swivel hinge body comprising:
     two forks extending in a plane parallel from the swivel hinge body; and
     a lower lip extending from the swivel hinge body in parallel with the two forks;
   a swivel pin; and
   a swivel block positioned between the lower lip and the plane of the two forks and held in place by the swivel pin such that the swivel block is able to rotate in an arc with respect to the lower lip and the swivel hinge body, the swivel block comprising a swivel block face;
   wherein the entire swivel block face fits completely flush against an edge of a component of the EBF device such that, when the tensioning mechanism is applying tension to the wire, the swivel hinge body is prevented from deflecting from an angle formed by the wire and the edge.

2. The device of claim 1, wherein the tensioning mechanism is a ratchet device.

3. The device of claim 1, wherein the component of the EBF device is a plate.

4. The device of claim 1, wherein the component of the EBF device is a post.

5. The device of claim 1, wherein the component of the EBF device is a ring.

6. The device of claim 1, wherein a distance between the forks is sufficient both to fit around a fixation bolt of the EBF device and to prevent the fixation bolt from turning when the fixation bolt is secured to the component.

7. A swivel hinge for use with a tensioning device for tensioning a wire in conjunction with an external bone fixation (EBF) device, comprising:
   a swivel hinge body for attachment to a tensioning mechanism, the swivel hinge body comprising:
     two forks extending in a plane parallel from the swivel hinge body; and
     a lower lip extending from the swivel hinge body in parallel with the two forks;
   a swivel pin; and
   a swivel block positioned between the lower lip and the plane of the two forks and held in place b the swivel pin such that the swivel block is able to rotate in an arc with respect to the lower lip and the swivel hinge body, the swivel block comprising a swivel block face;
   wherein the swivel face fits completely flush against an edge of a component of the EBF device such that, when the tensioning mechanism is applying tension to the wire, the swivel hinge body is prevented from deflecting from an angle formed by the wire and the edge.

8. The device of claim 7, wherein the tensioning mechanism is a ratchet device.

9. The device of claim 7, wherein the component of the EBF device is a plate.

10. The device of claim 7, wherein the component of the EBF device is a post.

11. The device of claim 7, wherein the component of the EBF device is a ring.

12. The device of claim 7, wherein a distance between the forks is sufficient both to fit around a fixation bolt of the EBF device and to prevent the fixation bolt from turning when the fixation bolt is secured to the component.

* * * * *